(12) United States Patent
Tsukamoto

(10) Patent No.: US 12,256,973 B2
(45) Date of Patent: Mar. 25, 2025

(54) BALLOON ABLATION CATHETER SYSTEM AND METHOD OF CONTROLLING SAME

(71) Applicant: Toray Industries, Inc., Tokyo (JP)

(72) Inventor: Kota Tsukamoto, Tokyo (JP)

(73) Assignee: Toray Industries, Inc., Tokyo (JP)

( * ) Notice: Subject to any disclaimer, the term of this patent is extended or adjusted under 35 U.S.C. 154(b) by 437 days.

(21) Appl. No.: 17/915,052

(22) PCT Filed: Mar. 31, 2021

(86) PCT No.: PCT/JP2021/013837
§ 371 (c)(1),
(2) Date: Sep. 27, 2022

(87) PCT Pub. No.: WO2021/201101
PCT Pub. Date: Oct. 7, 2021

(65) Prior Publication Data
US 2023/0157741 A1 May 25, 2023

(30) Foreign Application Priority Data
Mar. 31, 2020 (JP) .................. 2020-063087

(51) Int. Cl.
*A61B 18/08* (2006.01)
*A61B 17/00* (2006.01)
(Continued)

(52) U.S. Cl.
CPC .. *A61B 18/082* (2013.01); *A61B 2017/00199* (2013.01); *A61B 2017/00292* (2013.01);
(Continued)

(58) Field of Classification Search
None
See application file for complete search history.

(56) References Cited

U.S. PATENT DOCUMENTS 5,496,311 A * 3/1996 Abele ................. A61B 18/082
606/28
5,868,736 A 2/1999 Swanson et al.
(Continued)

FOREIGN PATENT DOCUMENTS

EP 3 117 791 A1 1/2017
JP 5-500179 A 1/1993
(Continued)

OTHER PUBLICATIONS

Extended European Search Report dated Mar. 19, 2024, of counterpart European Patent Application No. 21779546.7.
(Continued)

*Primary Examiner* — Linda C Dvorak
*Assistant Examiner* — Nicholas S Borsch
(74) *Attorney, Agent, or Firm* — DLA Piper LLP (US)

(57) ABSTRACT

An ablation catheter system includes: a catheter shaft; a balloon attached to the catheter shaft; a lumen extending through the catheter shaft in a longitudinal direction thereof and communicating with the interior of the balloon; a heating electrode and a temperature sensor provided in the interior of the balloon; a heater that applies electrical energy to the heating electrode; a pressure sensor; a balloon volume sensor; and a processor that calculates the estimated depth of ablation, using as variables, heating temperature of a generator, ablation time of the generator, a value of balloon pressure obtained from the pressure sensor and a value of balloon volume obtained from the balloon volume sensor.

5 Claims, 7 Drawing Sheets

(51) Int. Cl.
*A61B 18/00* (2006.01)
*A61B 90/00* (2016.01)

(52) U.S. Cl.
CPC ............... *A61B 2018/0022* (2013.01); *A61B 2018/00577* (2013.01); *A61B 2018/00648* (2013.01); *A61B 2018/00684* (2013.01); *A61B 2018/00791* (2013.01); *A61B 2090/063* (2016.02); *A61B 2090/064* (2016.02)

(56) References Cited

U.S. PATENT DOCUMENTS

| | | |
|---|---|---|
| 10,111,607 B2 | 10/2018 | Leo et al. |
| 2003/0065371 A1 | 4/2003 | Satake |
| 2010/0174279 A1 | 7/2010 | Satake |
| 2011/0264085 A1 | 10/2011 | Satake |
| 2012/0029504 A1 | 2/2012 | Afonso et al. |
| 2014/0371736 A1* | 12/2014 | Levin ................. A61B 18/04 606/28 |

FOREIGN PATENT DOCUMENTS

| | | |
|---|---|---|
| JP | 2003-102850 A | 4/2003 |
| JP | 2010-240004 A | 10/2010 |
| JP | 2010-259810 A | 11/2010 |
| JP | 2014-504896 A | 2/2014 |
| WO | 2010/070766 A1 | 6/2010 |
| WO | 2019/023280 A1 | 1/2019 |

OTHER PUBLICATIONS

International Search Report dated Jun. 1, 2021, of corresponding International Application No. PCT/JP2021/013837 along with an English translation.

* cited by examiner

BALLOON ABLATION CATHETER SYSTEM AND METHOD OF CONTROLLING SAME

TECHNICAL FIELD

This disclosure relates to an ablation catheter system with a balloon, capable of estimating the depth of ablation at the time of performing ablation, and a method of controlling the same.

BACKGROUND

Catheter ablation therapy is a treatment method in which an ablation catheter is inserted into a cardiac chamber, and myocardial tissue causing an arrhythmia or the like is destroyed by a method such as ablation. Catheter ablation is performed mainly for the treatment of tachyarrhythmias such as paroxysmal supraventricular tachycardia, atrial tachycardia, atrial flutter and paroxysmal ventricular tachycardia, and is a treatment method in which: the mechanism of origin and the site of origin of an arrhythmia are diagnosed by a cardiac electrophysiological examination; thereafter, an ablation catheter is inserted to reach the site of origin of the arrhythmia from the inside of the cardiac chamber; and the target site is destroyed by a method such as, for example, heating the distal end of the catheter.

Various catheters have been developed as ablation catheters for use in that treatment method. Examples of known catheters include: an ablation catheter which includes a metal electrode having a length of 4 mm to 8 mm and a diameter of 2 mm to 3 mm at the distal end portion of the catheter, and which isolates the site of origin of an arrhythmia by bringing the metal electrode portion into contact with the myocardial tissue causing the arrhythmia, in points; and an ablation catheter with a balloon in which a balloon is attached to the distal end of the catheter, and which is capable of heating the balloon within a cardiac atrium.

Since it is important to achieve a desired depth of ablation to carry out catheter ablation therapy effectively, it is required to accurately estimate the depth of ablation of the myocardial tissue which comes into contact with the balloon when using the above-described ablation catheter with a balloon.

JP 2010-259810 A discloses a catheter comprising a metal electrode at the distal end portion of the catheter, and is capable of providing the estimated size of the lesion site (depth, volume or area) in real time, by measuring the force applied to the target tissue, and integrating the measured force over the energization time of the ablation probe.

JP 2003-102850 A and JP 2010-240004 A each disclose an ablation catheter system with a balloon including an ablation catheter having a balloon at the distal end of the catheter tube, and a high frequency generator and a device for homogenizing the balloon surface temperature.

In the catheter disclosed in JP 2010-259810 A, it is possible to estimate the contact resistance with the target tissue and to provide the size of the lesion site in real time when ablating the target tissue directly by high frequency energization, by energizing the ablation head provided at the distal end portion of the catheter and by measuring the contact force applied to the ablation head itself. In the ablation using a balloon, on the other hand, tissue is ablated by the thermal conduction of the balloon heated by a heating device, and therefore, the method disclosed in JP 2010-259810 A cannot be directly used in the estimation of the depth of ablation in the balloon catheter.

In JP 2003-102850 A and JP 2010-240004 A, a high-frequency heating balloon catheter has been reported which is capable of heating by high frequency the tissue which comes into contact with the balloon homogeneously as much as possible, and safely performing a hyperthermia treatment on an affected area at an optimal temperature. Although JP 2003-102850 A and JP 2010-240004 A show examples of when the depth of ablation of the tissue is proportional to the balloon contact temperature and the energization time of the high frequency, the depth of ablation varies depending on the contact state between the balloon and the tissue even if the balloon surface temperature is constant, possibly resulting in a failure to perform a sufficient ablation.

SUMMARY

I provide (1) to (7):

(1) An ablation catheter system comprising:
a catheter shaft;
a balloon attached to the catheter shaft;
a lumen extending through the catheter shaft in the longitudinal direction thereof and communicating with the interior of the balloon;
a heating electrode and a temperature sensor provided in the interior of the balloon;
a heating device that applies electrical energy to the heating electrode;
a pressure sensor;
a balloon volume sensor; and
a processor that calculates the estimated depth of ablation, using as variables, the heating temperature of a generator, the ablation time of the generator, the value of the balloon pressure obtained from the pressure sensor and the value of the balloon volume obtained from the balloon volume sensor.

(2) The ablation catheter system according to (1), wherein the estimated depth of ablation is determined from a reference table based on the heating temperature, the ablation time and the balloon volume, and from a mathematical expression that correlates with the balloon pressure.

(3) The ablation catheter system according to (2), wherein the mathematical expression is equation (1):

$$D=k*P^2+k'*P+t \qquad (1)$$

wherein D represents the estimated depth of ablation; each of k and k' represents the constant of proportionality referenced from the reference table based on the balloon volume, the heating temperature and the ablation time; t represents a constant referenced from the reference table based on the balloon volume, the heating temperature and the ablation time; and P represents the value of the balloon pressure.

(4) The ablation catheter system according to any one of (1) to (3), comprising a display device capable of displaying the estimated depth of ablation output from the processor.

(5) The ablation catheter system according to any one of (1) to (4), wherein the pressure sensor is provided on the surface of the balloon or in the interior of the balloon.

(6) The ablation catheter system according to any one of (1) to (5), wherein the processor outputs the heating temperature and the ablation time necessary for achieving the estimated depth of ablation that has been set, depending on the obtained values of the balloon pressure and the balloon volume.

(7) A method of controlling an ablation system, the method comprising:
measuring the balloon pressure;
measuring the balloon volume; and estimating the depth of ablation based on the data of the heating temperature of the generator, the ablation time of the generator, the balloon pressure and the balloon volume.

The ablation catheter system with a balloon and the method of controlling the same allow for estimating the depth of ablation at the time of performing ablation, from the settings of the balloon pressure, the balloon volume, the heating temperature and the ablation time, thereby enabling to reliably ablate the affected area.

REFERENCE SIGNS LIST

Figure 1:
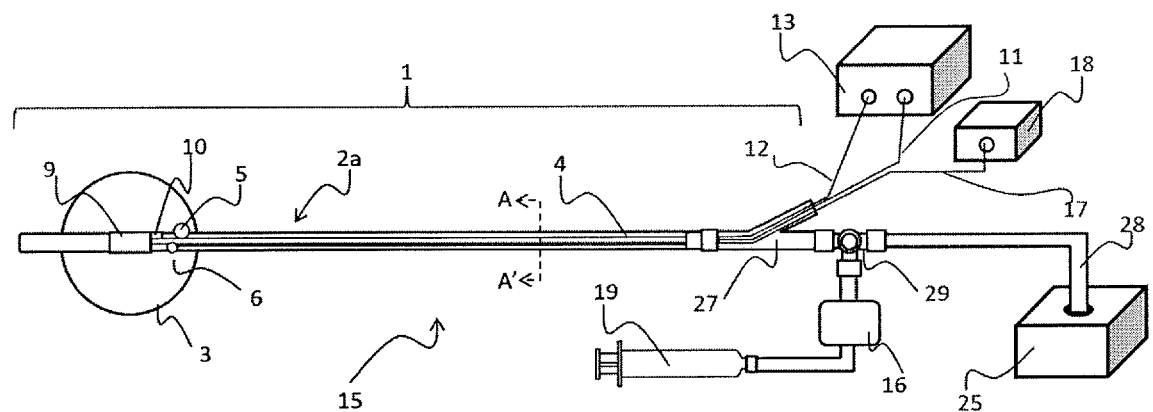
FIG. 1 is a schematic view of a balloon catheter according to a first example.

1 ablation catheter with a balloon
2 catheter shaft (2a, 2b, 2c)
3 balloon
4 lumen
5 side hole at distal end portion
6 pressure sensor
9 heating electrode
10 temperature sensor
11 heating electrode lead wire
12 temperature sensor lead wire
13 heating device
14 heating liquid
15 ablation catheter system with a balloon
16 balloon volume sensor
17 pressure sensor lead wire
18 pressure measurement unit
19 syringe
20 inner tube
21 outer tube
22 central lumen
23 guide wire
25 vibration application device
26 processor
27 handle
28 extension tube
29 three-way stopcock
42 water tank
43 counter electrode plate
44 ablation test device
45 porcine myocardium
46 funnel (for holding porcine myocardium)
47 contact pressure sensor

DETAILED DESCRIPTION

Preferred examples will be described below in specific detail with reference to the accompanying drawings. However, my systems and methods are in no way limited to these examples. The same reference numerals denote the same elements, and redundant descriptions are omitted. Further, the ratios in the drawings do not necessarily match those in the descriptions.

My ablation catheter system comprises:
a catheter shaft;
a balloon attached to the catheter shaft;
a lumen extending through the catheter shaft in the longitudinal direction thereof and communicating with the interior of the balloon;
a heating electrode and a temperature sensor provided in the interior of the balloon;
a heating device that applies electrical energy to the heating electrode;
a pressure sensor;
a balloon volume sensor; and
a processor that calculates the estimated depth of ablation, using as variables, the heating temperature of a generator, the ablation time of the generator, the value of the balloon pressure obtained from the pressure sensor and the value of the balloon volume obtained from the balloon volume sensor.

The term "depth of ablation" refers to the distance (mm) in the vertical direction from the outermost surface of the target tissue to be ablated with which the balloon is brought into contact, to the deepest plane of the target tissue in which irreversible denaturation has occurred.

Further, the term "balloon pressure" refers to the "balloon internal pressure" applied to the interior of the balloon, or the "balloon contact pressure" which is the pressure generated due to the pressing of the balloon against the target tissue to be ablated.

An ablation catheter 1 with a balloon according to the first example will be described with reference to FIG. 1.

An ablation catheter system 15 with a balloon shown in FIG. 1 is largely constituted by: the ablation catheter 1 with a balloon; a pressure measurement section composed of a pressure sensor 6 for measuring the balloon pressure, and a pressure measurement unit 18; a liquid adjustment section composed of a balloon volume sensor 16, a syringe 19 and a vibration application device 25; and a heating device 13 that supplies electric power to a heating electrode 9.

The ablation catheter 1 with a balloon comprises a balloon 3 capable of being inflated and deflated, at the distal end side of a catheter shaft 2a, and the distal end portion and the proximal end portion of the balloon 3 are fixed to the catheter shaft 2a. The catheter shaft 2a includes a lumen 4 which extends through the interior thereof, and the lumen 4 communicates with the interior of the balloon 3 at the distal end portion of the catheter shaft 2a through a side hole 5 provided in the interior of the balloon 3. The lumen 4 at the proximal end side of the catheter shaft 2a is connected to the balloon volume sensor 16 through a three-way stopcock 29, and the balloon volume sensor 16 is connected to the vibration application device 25 through an extension tube 28. The heating electrode 9 is fixed to the catheter shaft 2a in the interior of the balloon 3, and a temperature sensor 10 is fixed to the proximal end of the heating electrode 9. A heating electrode lead wire 11 connected to the heating electrode 9 and a temperature sensor lead wire 12 connected to the temperature sensor 10 are inserted through the lumen 4 and connected to the heating device 13. The pressure sensor 6 is connected to a pressure sensor lead wire 17, and then connected to the pressure measurement unit 18.

The pressure sensor 6 is preferably provided on the surface of the balloon 3, in the interior of the balloon 3 or within the lumen 4. In the ablation catheter 1 with a balloon according to the first example shown in FIG. 1, the pressure sensor 6 is provided in the interior of the balloon 3 and within the lumen 4.

The catheter shaft 2a preferably has a length of 0.5 m to 2 m, from the viewpoint of allowing the balloon 3 to reach the myocardial tissue.

Further, the catheter shaft 2a preferably has a diameter of 3 mm to 5 mm, from the viewpoint of being inserted into a blood vessel.

The catheter shaft 2a is preferably made of a flexible material having an excellent antithrombogenicity. Examples of the flexible material having an excellent antithrombogenicity include fluoropolymers, polyamides, polyurethane polymers and polyimides, but not limited thereto.

The balloon 3 is required to have a shape capable of conforming to a blood vessel fittingly so that the balloon can adhere to the site of origin of an arrhythmia in close contact. For example, the balloon 3 having a size that conforms to the left atrium-pulmonary vein junction is preferably one having a spherical shape with a diameter of 15 mm to 40 mm. The definition of the spherical shape includes those in the forms of a true sphere, an oblate spheroid and a prolate spheroid. However, a balloon in the form of a true sphere is preferred. Further, the definition of these spherical shapes also includes those that are roughly spherical.

The balloon 3 preferably has a film thickness of 20 μm to 100 μm.

The balloon 3 is preferably made of an elastic material having an excellent antithrombogenicity, and more preferably a polyurethane-based polymeric material.

Examples of the polyurethane-based polymeric material include thermoplastic polyether urethane, polyether polyurethane urea, fluorine polyether urethane urea, polyether polyurethane urea resins and polyether polyurethane urea amide.

Figure 2:
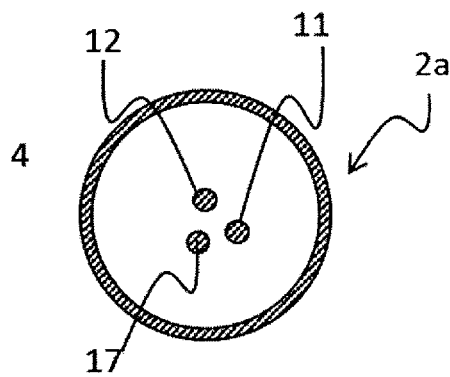
FIG. 2 is a cross-sectional view showing a cross section taken along the line A-A' of the balloon catheter shown in FIG. 1.
Figure 3:
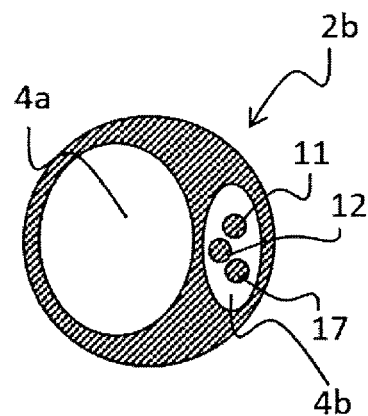
FIG. 3 is a cross-sectional view showing a cross section taken along the line A-A' in a modified example of the first example.

As shown in FIG. 2, the structure of the catheter shaft according to the first example is a structure in which the heating electrode lead wire 11, the temperature sensor lead wire 12 and the pressure sensor lead wire 17 are inserted through the lumen of the catheter shaft 2a, and a heating liquid 14 passes through the gap in the interior of the lumen and between the respective lead wires. As a modified example of the structure of the catheter shaft, the catheter shaft may have a structure such as that of a catheter shaft 2b with double lumens, as shown in FIG. 3, wherein the catheter shaft 2b comprises a lumen 4a through which the heating liquid 14 communicating with the interior of the balloon 3 passes, and a lumen 4b through which the heating electrode lead wire 11, the temperature sensor lead wire 12 and the pressure sensor lead wire 17 are inserted.

The measurement by the pressure sensor 6 is carried out, for example, by a method such as a resistance wire system or an electrostatic capacitive system, but not limited thereto.

Figure 4:
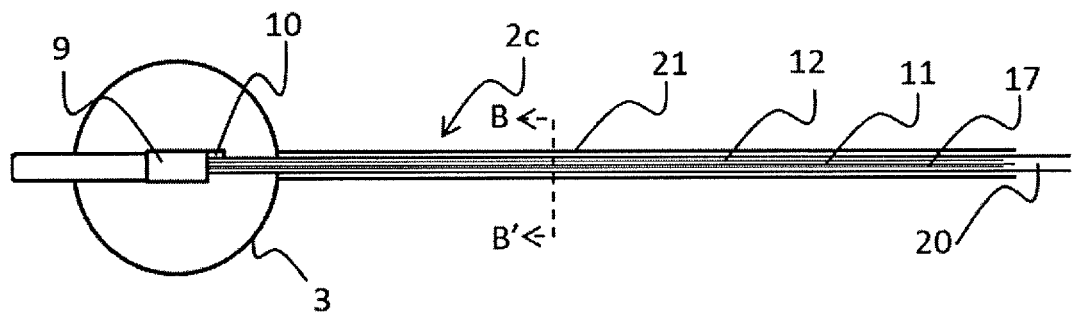
FIG. 4 is a schematic view showing the vicinity of the balloon in another modified example of the first example.
Figure 5:
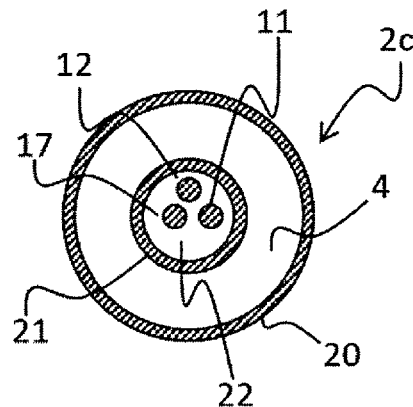
FIG. 5 is a cross-sectional view showing a cross section taken along the line B-B' of the balloon catheter shown in FIG. 4.
Figure 6:
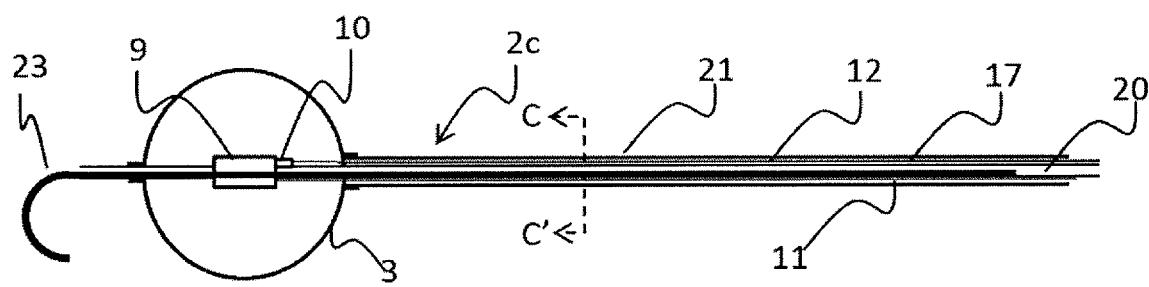
FIG. 6 is a schematic view showing the vicinity of the balloon in yet another modified example of the first example.
Figure 7:
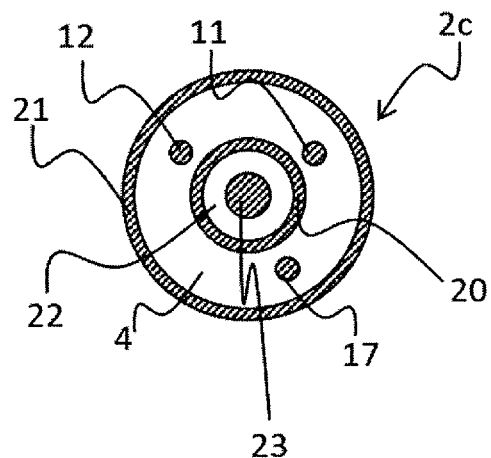
FIG. 7 is a cross-sectional view showing a cross section taken along the line C-C' of the balloon catheter shown in FIG. 6.

Further, as shown in FIG. 4 or 6, the catheter shaft may be a catheter shaft 2c of a dual lumen type, in which an inner tube 20 is inserted into the lumen of an outer tube 21. In the catheter shaft 2c of a dual lumen type shown in FIG. 4, the catheter shaft 2c preferably has a structure as shown in FIG. 5, in which: the space between the outer tube 21 and the inner tube 20 communicates with the interior of the balloon 3; the pressure sensor 6 is provided on the surface of the balloon 3, in the interior of the balloon 3 or within the lumen 4; and the heating electrode lead wire 11 and the temperature sensor lead wire 12 are inserted through the lumen of the inner tube 20. In the catheter shaft 2c of a dual lumen type shown in FIG. 6, the catheter shaft 2c preferably has a structure as shown in FIG. 7, in which: the space between the outer tube 21 and the inner tube 20 communicates with the interior of the balloon 3; the pressure sensor 6 is provided on the surface of the balloon 3, in the interior of the balloon 3 or the space between the outer tube 21 and the inner tube 20; the heating electrode lead wire 11, the temperature sensor lead wire 12 and the pressure sensor lead wire 17 are inserted through the space between the outer tube 21 and the inner tube 20; and a guide wire 23 is inserted through a central lumen 22 of the inner tube 20.

In the catheter shaft 2c of a dual lumen type, it is preferred, as shown in FIG. 4 or 6, that the distal end portion of the balloon 3 be fixed to the distal end portion in the longitudinal direction of the inner tube 20, and that the proximal end portion of the balloon 3 be fixed to the distal end portion in the longitudinal direction of the outer tube 21.

The heating electrode 9 preferably has a tubular shape, for example, in the form of a coil or a cylinder with a length of 10 mm to 20 mm.

The electrical wire of the heating electrode 9 in the form of a coil preferably has a diameter of 0.1 mm to 1 mm, from the viewpoint of practical use.

Examples of the material of the heating electrode 9 include gold, silver, platinum and copper, and alloys of these metals.

The heating electrode lead wire 11 connected to the heating electrode 9 is inserted through the lumen 4, and connected to the heating device 13.

The heating electrode lead wire 11 preferably has a diameter of 0.1 mm to 1 mm, from the viewpoint of practical use.

Examples of the material of the heating electrode lead wire 11 include copper, silver, gold, platinum and tungsten, and alloys of these metals. Further, the heating electrode lead wire 11 is preferably provided with an electrically insulating protective coating made of a fluororesin or the like, from the viewpoint of preventing the occurrence of short circuits.

The heating device 13 is preferably a high frequency generator, and the frequency of the high frequency current to be supplied to the heating electrode 9 is preferably 100 kHz or more, from the viewpoint of preventing the patient from getting an electric shock.

A processor 26 in the heating device typically comprises a general-purpose computer processor that includes front-end and interface circuits suitable for receiving signals from the ablation catheter 1 with a balloon. The processor 26 can be programmed in software to execute the functions described herein. Further, one or more components included in the heating device 13 may be configured as separate hardware, or may be configured to share a part therebetween. At least a part of the heating device 13 may be constituted by software. A part of the heating device 13 may be arranged at a position physically spaced apart from the heating device. The heating device 13 may also be configured such that a part of the components thereof is capable of working together with another component(s) through communication via a network. Alternatively, the heating device 13 may be configured as a device in which a part of the components thereof is capable of communicating with another component(s) through an external network. For example, a part of the heating device 13 may be present on a server on the cloud or on a database.

The temperature sensor 10 is preferably fixed to the heating electrode 9 or the catheter shaft 2a from the viewpoint of stably measuring the internal temperature of the balloon 3. However, the temperature sensor 10 may be fixed to the inner surface of the balloon 3, from the viewpoint of measuring the surface temperature of the balloon 3.

The temperature sensor 10 may be, for example, a thermocouple or a resistance temperature detector.

The temperature sensor lead wire 12 connected to the temperature sensor 10 is inserted through the lumen 4, and connected to a temperature control unit.

The temperature sensor lead wire 12 preferably has a diameter of 0.05 mm to 0.5 mm, from the viewpoint of practical use.

When the temperature sensor 10 is a resistance temperature detector, examples of the material of the temperature sensor lead wire 12 include copper, silver, gold, platinum and tungsten, and alloys of these metals. Further, the temperature sensor lead wire 12 is preferably provided with an electrically insulating protective coating made of a fluororesin or the like, from the viewpoint of preventing the occurrence of short circuits. When the temperature sensor 10 is a thermocouple, the temperature sensor lead wire 12 is preferably made of the same material as the thermocouple, and examples of the material include copper and constantan in a T-type thermocouple, and chromel and alumel in a K-type thermocouple.

The pressure sensor 6 is connected to the pressure measurement unit 18, and the pressure measurement unit 18 is connected to the heating device 13. The same material as that of the temperature sensor lead wire 12 can be used as the material of the pressure sensor lead wire 17.

It is preferred to use a contrast medium or a contrast medium diluted with physiological saline as the heating liquid 14, from the viewpoint of observing the inflated balloon 3 in an X-ray fluoroscopic image. In supplying a high frequency current to the heating electrode 9, an ionic contrast medium or a contrast medium diluted with physiological saline is preferred, because of having an electrical conductivity.

The syringe 19 communicates with the extension tube 28, and with the balloon 3 through the lumen 4. In addition to the syringe 19, any device may be used, as a device which is used for injecting and suctioning a liquid into and from the interior of the balloon 3, and which is disposed outside the ablation catheter 1 with a balloon. To stabilize the heating temperature of the balloon 3, however, such a device is preferably the vibration application device 25 that repeatedly suctions and discharges a microvolume of the heating liquid to apply vibration to the liquid within the balloon 3. By applying vibration to the heating liquid within the balloon, the liquid filled in the interior of the balloon 3 is stirred, allowing the surface temperature of the balloon to be more easily maintained homogeneously.

The vibration application device 25 that applies vibration to the heating liquid within the balloon may be, for example, a device including a roller pump, a diaphragm pump, a bellows pump, a vane pump, a centrifugal pump, or a pump composed of a combination of a piston and a cylinder.

Figure 8:
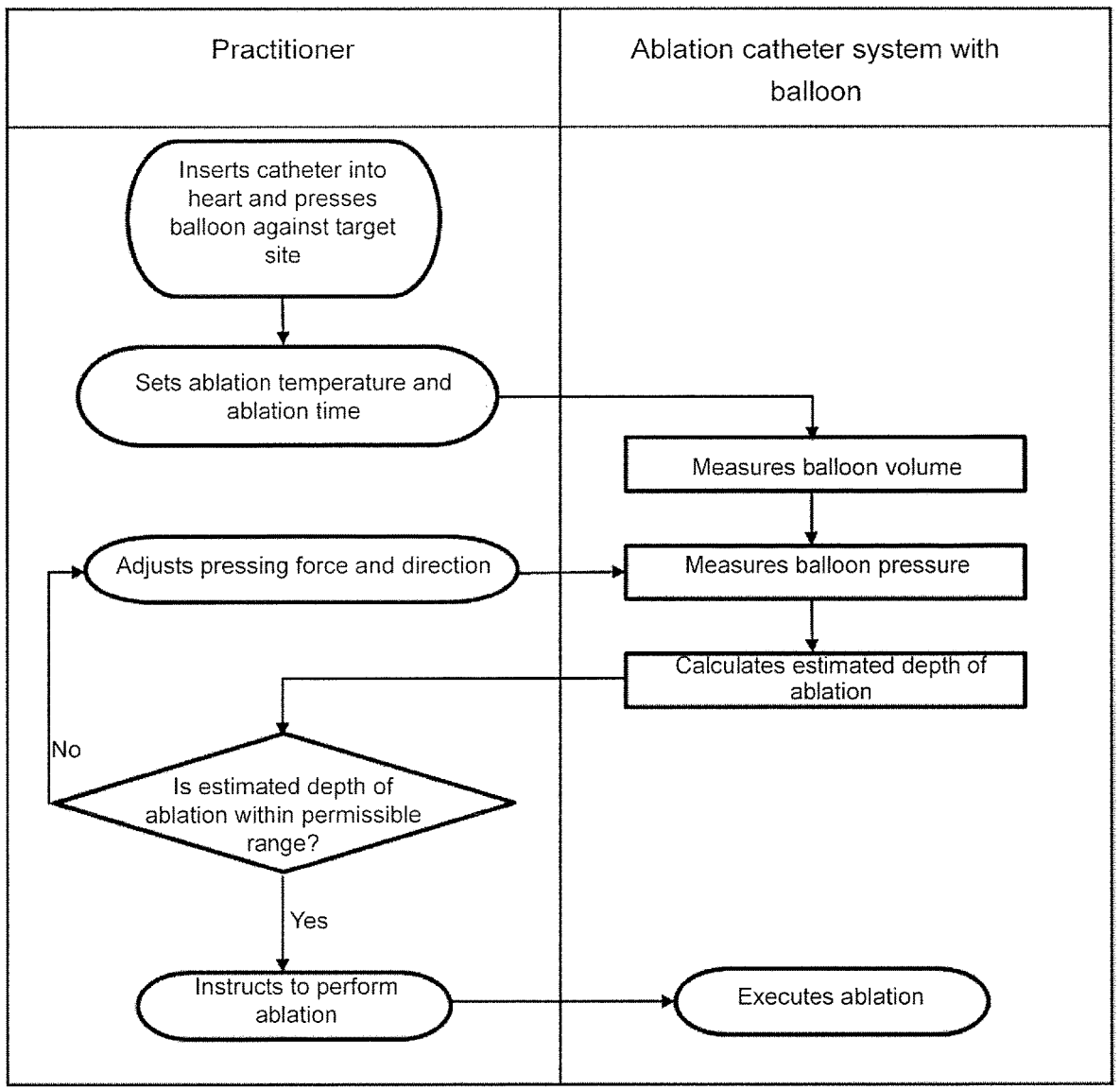
FIG. 8 is a flow chart related to the control of the ablation catheter system with a balloon.

In some examples, the estimated depth of ablation is determined from a specific reference table based on the heating temperature, the ablation time and the balloon volume, and from a mathematical expression that correlates with the balloon pressure selected from the reference table. As an example, FIG. 8 shows a flow chart illustrating the procedure for controlling the ablation catheter system with a balloon by a physician, and for using the same. In the ablation procedure, the physician first inserts the catheter into the heart, and presses the balloon against the target site. Thereafter, the physician sets the numerical values of the heating temperature and the ablation time to the ablation catheter system with a balloon. The processor in the ablation catheter system with a balloon calculates the balloon volume from the injection volume into the balloon, and the pressure is measured when the balloon has come into contact with the tissue and the physician fixed the position of the balloon. Based on the thus set values and measured values, the estimated depth of ablation by the ablation using the ablation catheter with a balloon, which is to be carried out subsequently, can be calculated by the following method.

Since the estimated depth of ablation (D) correlates with the balloon pressure (P), at each of the heating temperature, the ablation time and the balloon volume, the estimated depth of ablation is calculated from equation (1):

$$D=k*P^2+k'*P+t \tag{1}$$

wherein D represents the estimated depth of ablation; each of k and k' represents the constant of proportionality selected from the reference table based on the heating temperature, the ablation time and the balloon volume; t represents a constant selected from the reference table based on the heating temperature, the ablation time and the balloon volume; and P represents the value of the balloon pressure.

The estimated depth of ablation (D) can be calculated using either the balloon internal pressure or the balloon contact pressure as the balloon pressure (P). In addition, the estimated depth of ablation (D) can be calculated using a reference table corresponding to each of the balloon internal pressure and the balloon contact pressure, as the reference table.

As the reference table showing the relationship between the heating temperature, ablation time and balloon volume with the constant of proportionality k and constant t, it is possible to use one prepared in advance, and stored in the processor or a recording medium.

For example, when the heating temperature is 73° C., the ablation time is 3 minutes and the balloon volume is 10 mL, the values k=0, k'=0.084 and t=0.59 can be obtained, by referring to the numerical values in the reference table stored in the processor in advance. When these values are substituted into equation (1), the estimation equation is represented by equation (2). By substituting the value of the balloon volume measured by the measuring device into this estimation equation, the estimated depth of ablation (D) can be obtained.

$$D=0.084*P+0.59 \tag{2}$$

The thus obtained estimated depth of ablation (D) is displayed to the physician carrying out the ablation procedure, using a display device such as a display. The physician can perform various treatments using the estimated depth of ablation, to achieve the target depth of ablation. For example, the physician can achieve the target depth of ablation by adjusting the heating temperature, the ablation time, the balloon volume and the balloon pressure.

Figure 9:
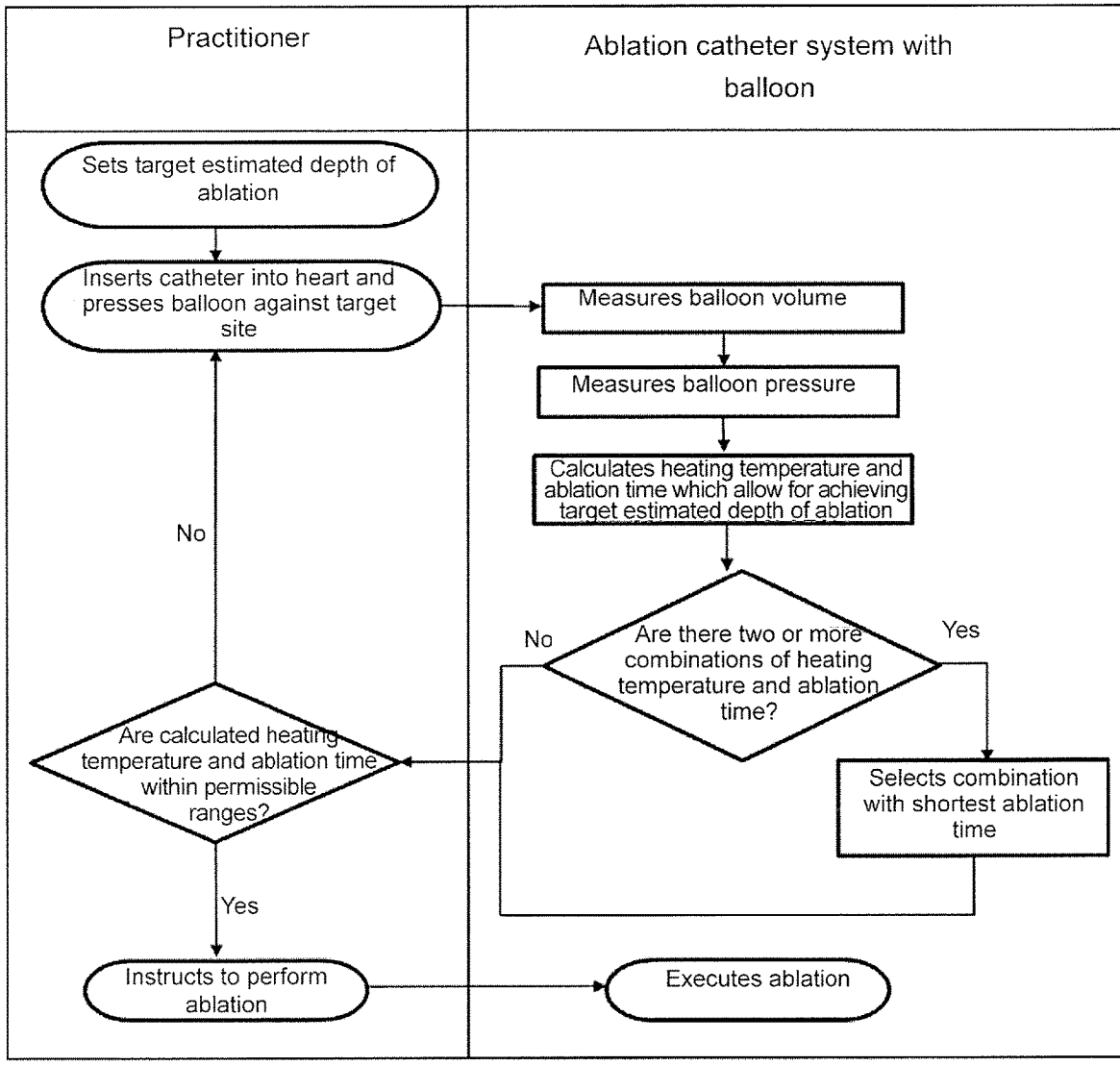
FIG. 9 is a flow chart showing the procedure of controlling the ablation catheter system with a balloon.

In another example, the processor can output, in addition to the numerical value of the estimated depth of ablation, the heating temperature and the ablation time necessary to achieve the estimated depth of ablation that has been set, corresponding to the obtained values of the balloon pressure and the balloon volume, as shown in FIG. 9. At this time, when there is one combination of the necessary heating temperature and ablation time, the processor is configured to output the combination. When two or more combinations of the necessary heating temperature and ablation time have been calculated, the processor selects and outputs the combination with the shortest ablation time, from the calculated combinations.

In another example, the ablation catheter system may be configured such that, after the target estimated depth of ablation has been input, the processor calculates the heating temperature and the ablation time which allow to achieve the target estimated depth of ablation based on the balloon pressure and the balloon volume obtained by the measurement, and outputs the calculated results to the display device.

EXAMPLES

Specific Examples of my balloon catheter will now be described. The term "length" refers to the length in the longitudinal direction.

Production of Ablation Catheter System with Balloon

The balloon 3 made of polyurethane with a diameter of 30 mm and a thickness of 15 µm was produced by blow molding using a polyurethane tube.

A polyurethane tube with an outer diameter of 3.6 mm, an inner diameter of 3.0 mm and a length of 1000 mm was molded to prepare the outer tube 21. Further, a polyamide tube with an outer diameter of 1.6 mm, an inner diameter of 1.2 mm and a length of 1100 mm was molded to prepare the inner tube 20. A handle 27 was connected to the proximal ends of these tubes.

A copper wire with a diameter of 0.26 mm and a length of 1700 mm which had been provided with an electrically insulating coating film made of perfluoroalkoxy alkane was used as the heating electrode lead wire 11, and a constantan wire with a diameter of 0.13 mm and a length of 1500 mm which had been provided with an electrically insulating coating made of polytetrafluoroethylene was used as the temperature sensor lead wire 12.

A length of 200 mm of the electrically insulating coating film provided on the heating electrode lead wire 11 and 20 mm of the electrically insulating coating film provided on the temperature sensor lead wire 12 were peeled off. Taking the position 25 mm from the distal end of the inner tube 20 as the starting point, the heating electrode lead wire 11 was wound around the inner tube 20 in the form of a coil while sandwiching the temperature sensor lead wire 12 between the heating electrode lead wire 11 and the inner tube 20. At this time, the portion of the heating electrode lead wire 11 formed into a coil forms the heating electrode 9. At the same time, at the starting point of the lead wire wound in the form of a coil, the portions of the heating electrode lead wire 11 and the temperature sensor lead wire 12 where the electrically insulating coating films thereof have been peeled off were brought into contact with each other to form a thermocouple which is the temperature sensor 10. As a result, the heating electrode 9 in the form of a coil with a length of 13 mm and the temperature sensor 10 were formed on the inner tube 20. At the portions where the temperature sensor 10 had been formed, the heating electrode lead wire 11 and the temperature sensor lead wire 12 were welded together and fixed.

To prevent misalignment, polyurethane tubes were fixed on the inner tube 20 by heat welding, at the distal end and the proximal end of the heating electrode 9.

The pressure sensor 6 was fixed to the inner tube 20 with a polyurethane-based adhesive, at the proximal end side of the heating electrode 9 and the temperature sensor 10, and the pressure sensor lead wire 17 was connected thereto. The other end of the pressure sensor lead wire 17 was inserted through the lumen 4 and connected to the pressure measurement unit 18 via the handle 27. The balloon internal pressure can be measured by fixing the pressure sensor 6 to the inner tube 20 in this manner.

The balloon 3 was inserted from the distal end side of the inner tube 20, and the proximal end portion of the balloon 3 was fixed to the distal end portion of the outer tube 21 by heat welding, to form a portion at which the distal end of the outer cylindrical shaft and the proximal end portion of the balloon were fixed with each other. Further, the distal end portion of the balloon 3 was fixed to the inner tube 20 by heat welding.

The portions of the heating electrode lead wire 11 and the temperature sensor lead wire 12 on the proximal end side were inserted through the lumen 4 between the outer tube 21 and the inner tube 20 and through the interior of the handle 27, and connected to the heating device 13.

The three-way stopcock 29 was attached to the branching portion of the handle 27. Then the balloon volume sensor 16 was attached to one end of the three-way stopcock 29, the extension tube 28 was attached to the other end of the branching portion, and further, the extension tube 28 was connected to the vibration application device 25. This made it possible to measure the balloon volume, and to form a path through which the vibration from the vibration application device 25 is transmitted and applied to the liquid within the balloon 3 through the extension tube 28, handle 27 and the lumen 4 between the outer tube 21 and the inner tube 20. In this manner, the balloon catheter ("Example 1") of Example 1 was produced. As described above, Example 1 can measure the balloon internal pressure, the balloon volume and the heating temperature of the balloon 3.

Subsequently, the balloon catheter of Example 2 was produced as another example. The points of difference from Example 1 will be described below.

The pressure sensor 6 was attached on the surface of the balloon 3 with a polyurethane-based adhesive, and the pressure sensor lead wire 17 was attached to the pressure sensor 6. The pressure sensor lead wire 17 was prepared with the same specification as the temperature sensor lead wire 12, except that a copper wire was used as the material. The pressure sensor lead wire 17 was arranged in the same manner as the temperature sensor lead wire 12, and the other end thereof on the side of the hand was connected to the pressure measurement unit 18. By fixing the pressure sensor 6 on the surface of the balloon 3, in this manner, the balloon catheter of Example 2 ("Example 2") which is capable of measuring the balloon contact pressure instead of the balloon internal pressure was produced. As described above, Example 2 can measure the contact pressure, the balloon volume and the heating temperature of the balloon 3.

Preparation for Using Ablation Catheter System with Balloon

A mixed solution of a contrast medium (OMNIPAQUE (registered trademark), manufactured by Daiichi Sankyo Company Limited) and physiological saline in a volume ratio of 1:1, as the heating liquid 14, was supplied from the syringe to remove air from the interior of the balloon 3 and the lumen 4, and then the balloon 3 was inflated to a maximum diameter of 26 mm to 33 mm.

Evaluation of Balloon Internal Pressure and Depth of Ablation

Figure 10:
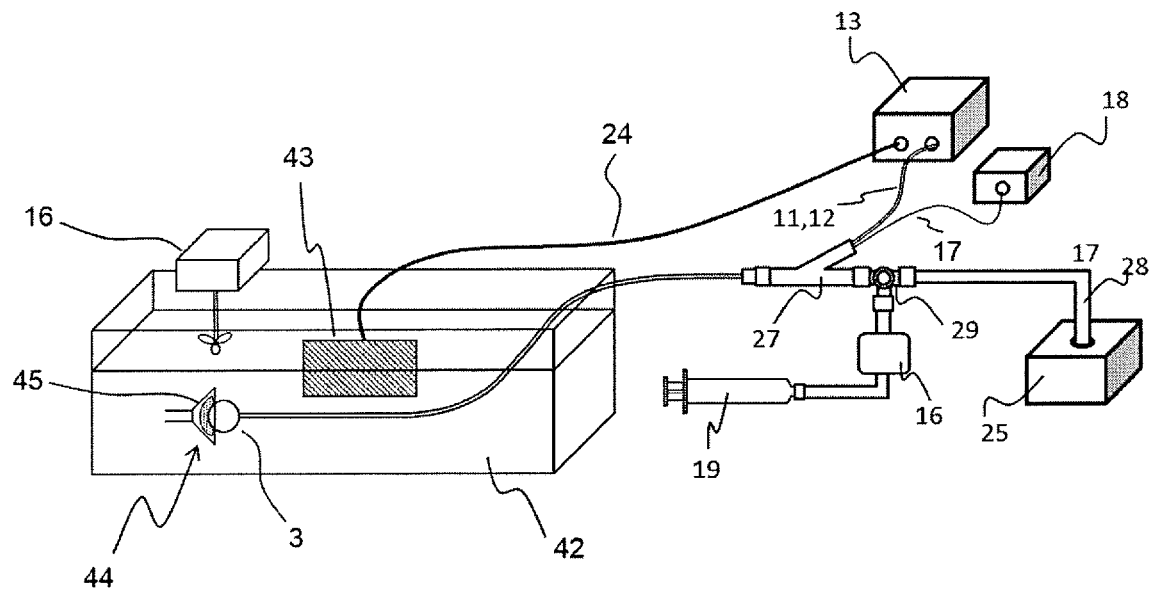
FIG. 10 is a schematic view showing an evaluation system of measuring the depth of ablation by the balloon catheter.

FIG. 10 shows an experimental system for evaluating the relationship between the balloon internal pressure and the depth of ablation, using the system of Example 1. After switching the three-way stopcock 29 to remove air from the interior of the extension tube 28, the three-way stopcock 29 was further switched to allow the pressure sensor 6 to communicate with the lumen 4.

A quantity of 35 L of physiological saline was introduced into a water tank 42, and maintained at 37° C. A plate-shaped electrode 43 (model number: 354; manufactured by Valley Lab, Inc.) which had been pasted on the inner wall of the water tank 42, and which is a counter electrode plate of the heating electrode 9, was connected to the heating device 13.

The balloon 3 of the ablation catheter 1 with a balloon was immersed in the water tank 42 in a state of being pressed against a myocardium 45 having a shape simulating a pulmonary vein, and the balloon internal pressure was measured.

The three-way stopcock 29 was switched to allow the vibration application device 25 to communicate with the lumen 4. The heating device 13 and the vibration application device 25 were activated simultaneously, the balloon 3 was heated at a heating temperature of 70° C., and the ablation was carried out for 180 seconds.

The ablated myocardium 45 was retrieved and incised, and the depth of ablation was measured using a scale or an image.

Figure 11:
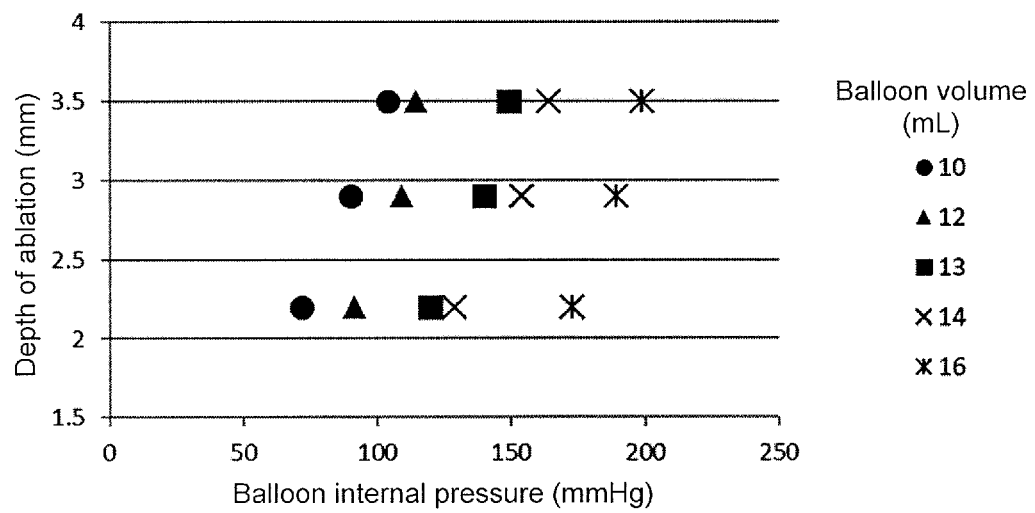
FIG. 11 is a graph showing the relationship between the balloon internal pressure and the depth of ablation.

FIG. 11 is a graph showing the relationship between the balloon internal pressure and the depth of ablation, at each balloon volume (mL), during the ablation using one example. The abscissa represents the balloon internal pressure (mmHg), and the ordinate represents the depth of ablation (mm).

The graph shown in FIG. 11 indicates that the depth of ablation and the balloon internal pressure correlates with each other, at each balloon volume. From the relationship between the depth of ablation and the balloon internal pressure at each balloon volume based on the figure, a reference table on their mutually correlated relationship was prepared. Further, it was possible to confirm that equation (1) holds true as the estimation equation for the depth of ablation, based on the mutually correlated relationship.

$$D=k*P^2+k'*P+t \quad (1)$$

wherein each of k and k' represents the constant of proportionality, and t represents a constant.

Evaluation of Balloon Contact Pressure and Depth of Ablation

Figure 12:
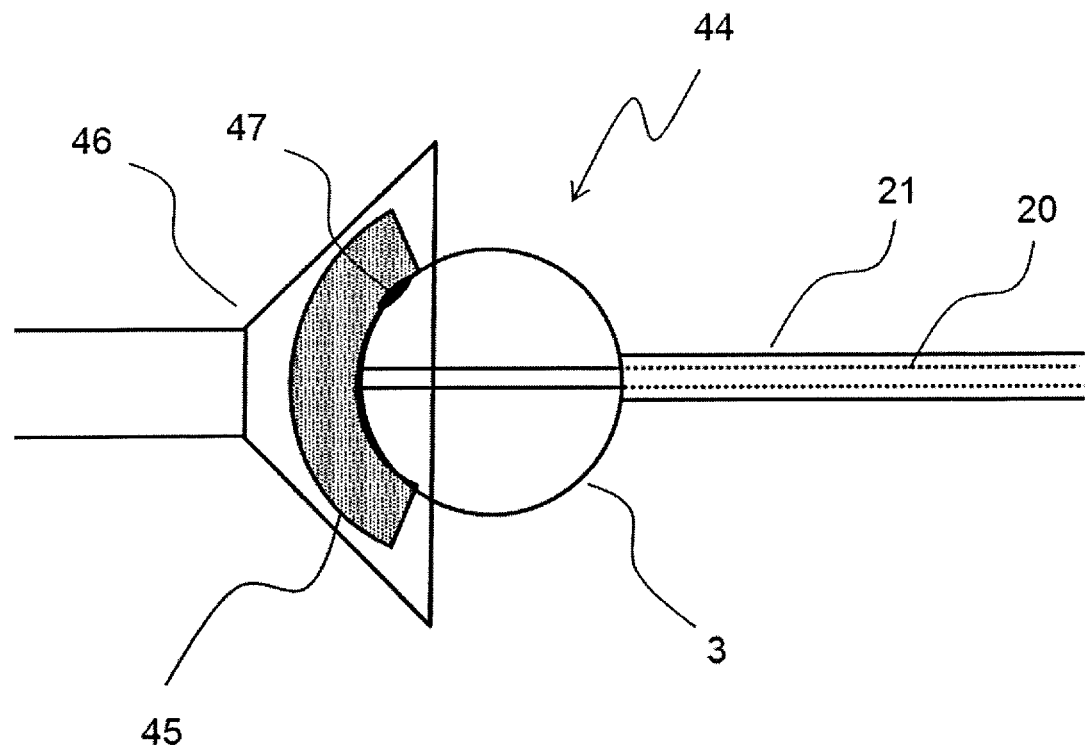
FIG. 12 is an enlarged schematic view showing the ablation site of the evaluation system shown in FIG. 10.

FIG. 12 shows an enlarged detailed view of the vicinity of the balloon, of an experimental system for evaluating the balloon contact pressure and the depth of ablation, using the system of Example 2. The overall arrangement is the same as that of FIG. 10. A quantity of 35 L of physiological saline was introduced into the water tank 42, and maintained at 37° C. The plate-shaped electrode 43 (model number: 354; manufactured by Valley Lab, Inc.) which had been pasted on the inner wall of the water tank 42, and which is a counter electrode plate of the heating electrode 9, was connected to the heating device 13.

The balloon 3 of the ablation catheter 1 with a balloon was immersed in the water tank 42 in a state of being pressed against the myocardium 45 having a shape simulating a pulmonary vein, and the balloon contact pressure was measured.

The vibration application device 25 was allowed to communicate with the lumen 4, the heating device 13 and the vibration application device 25 were activated simultaneously, the balloon 3 was heated at a heating temperature of 73° C., and the ablation was carried out for 180 seconds.

The ablated myocardium 45 was retrieved and incised, and the depth of ablation was measured using a scale or an image.

Figure 13:
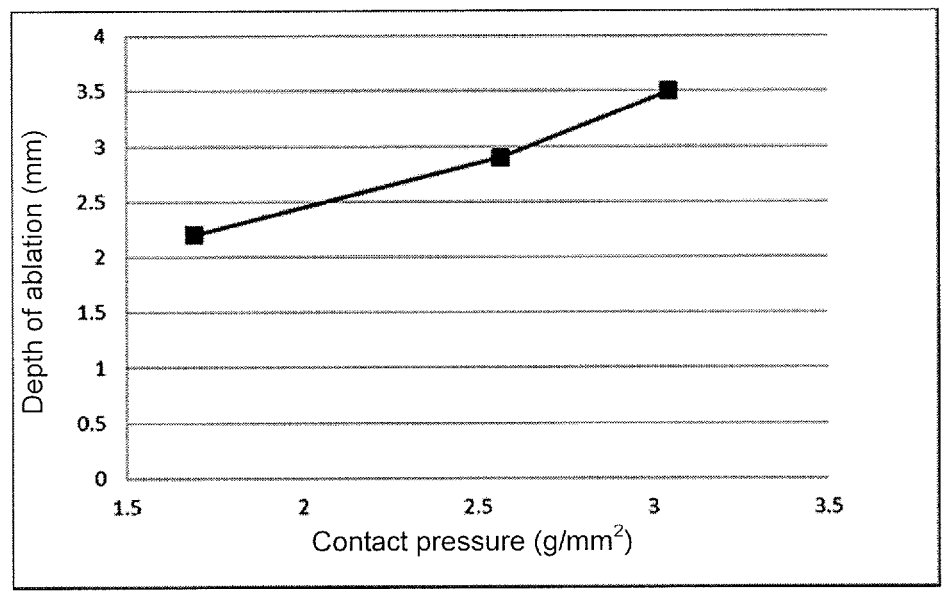
FIG. 13 is a graph showing the relationship between the contact pressure of the balloon and the depth of ablation.

FIG. 13 is a graph showing the relationship between the balloon contact pressure and the depth of ablation during the ablation, according to one example. The abscissa represents the balloon contact pressure, and the ordinate represents the depth of ablation.

The results of FIG. 13 revealed that the depth of ablation increases in correlation with the balloon contact pressure. Based on the results, it was possible to confirm equation (1) holds true:

$$D=k*P^2+k'*P+t \quad (1)$$

wherein each of k and k' represents the constant of proportionality, and t represents a constant.

It can be seen from the above-described results of the depth of ablation based on the ablation catheter systems of Examples 1 and 2, that, by inputting the relationship between the heating temperature, ablation time, balloon volume and balloon pressure with the depth of ablation, into the processor in advance, it is possible for a physician to know the estimated depth of ablation before starting the ablation, or alternatively, for the processor to control such that the depth of ablation intended by the physician is achieved.

INDUSTRIAL APPLICABILITY

I provide a balloon catheter for treating arrhythmias such as atrial fibrillation, endometriosis, cancer, hypertension or the like.

The invention claimed is:

1. An ablation catheter system comprising:
   a catheter shaft;
   a balloon attached to said catheter shaft;
   a lumen extending through said catheter shaft in a longitudinal direction thereof and communicating with the interior of said balloon;
   a heating electrode and a temperature sensor provided in the interior of said balloon;
   a heater that applies electrical energy to said heating electrode;
   a pressure sensor;
   a balloon volume sensor; and
   a processor that calculates the estimated depth of ablation, using as variables, heating temperature of a generator, ablation time of said generator, a value of balloon pressure obtained from said pressure sensor and a value of balloon volume obtained from said balloon volume sensor; wherein said estimated depth of ablation is determined from a reference table based on said heating temperature, said ablation time and said balloon volume, and from a mathematical expression that correlates with said balloon pressure; wherein said mathematical expression is equation (1): $D = k * p_2 + k'*P + t$ (1) wherein D represents said estimated depth of ablation; each of k and k' represents the constant of proportionality referenced from said reference table based on said balloon volume, said heating temperature and said ablation time; t represents a constant referenced from said reference table based on said balloon volume, said heating temperature and said ablation time; and P represents the value of said balloon pressure.

2. The ablation catheter system according to claim 1, further comprising a display device capable of displaying said estimated depth of ablation output from said processor.

3. The ablation catheter system according to claim 1, wherein said pressure sensor is provided on a surface of said balloon or in an interior portion of said balloon.

4. The ablation catheter system according to claim 1, wherein said processor outputs said heating temperature and said ablation time necessary to achieve the estimated depth of ablation that has been set, corresponding to the obtained values of said balloon pressure and said balloon volume.

5. A method of controlling an ablation system, the method comprising:
measuring the balloon pressure;
measuring the balloon volume; and estimating a depth of ablation based on data of a heating temperature of a generator, an ablation time of said generator, said balloon pressure and said balloon volume; wherein said estimated depth of ablation is determined from a reference table based on said heating temperature, said ablation time and said balloon volume, and from a mathematical expression that correlates with said balloon pressure; wherein said mathematical expression is equation (1): $D = k * P^2 + k'*P + t$ (1) wherein D represents said estimated depth of ablation; each of k and k' represents the constant of proportionality referenced from said reference table based on said balloon volume, said heating temperature and said ablation time; t represents a constant referenced from said reference table based on said balloon volume, said heating temperature and said ablation time; and P represents the value of said balloon pressure.

* * * * *